United States Patent [19]
Kissel et al.

[11] Patent Number: 5,929,196
[45] Date of Patent: Jul. 27, 1999

[54] POLYESTERS OF A POLYHYDROXYCARBOXYLIC ACID AND A POLYOL HAVING A SUBSTITUENT WITH ELECTROLYTE PROPERTIES

[75] Inventors: Thomas Kissel, Staufen; Youxin Li, Marburg, both of Germany

[73] Assignee: Schwarz Pharma AG, Monheim, Germany

[21] Appl. No.: 08/817,860

[22] PCT Filed: Feb. 23, 1995

[86] PCT No.: PCT/EP95/00655

§ 371 Date: Apr. 24, 1997

§ 102(e) Date: Apr. 24, 1997

[87] PCT Pub. No.: WO95/23175

PCT Pub. Date: Aug. 31, 1995

[30] Foreign Application Priority Data

Feb. 25, 1994 [DE] Germany ............... 44 06 172

[51] Int. Cl.⁶ ..................................... C08G 63/00
[52] U.S. Cl. ................... 528/271; 424/486; 528/176
[58] Field of Search ................. 528/176, 271; 514/420, 423, 576, 497, 78.05, 179; 424/486

[56] References Cited

U.S. PATENT DOCUMENTS

| | | | |
|---|---|---|---|
| 3,773,919 | 11/1973 | Boswell et al. | 424/19 |
| 4,937,254 | 6/1990 | Sheffield et al. | 424/497 |

FOREIGN PATENT DOCUMENTS

| | | |
|---|---|---|
| 0 058 481 | 10/1986 | European Pat. Off. . |
| 0 407 617 A1 | 1/1991 | European Pat. Off. . |
| 0 407 617 B1 | 1/1991 | European Pat. Off. . |
| 34 30 852 A1 | 3/1985 | Germany . |
| 2 145 422 | 3/1985 | United Kingdom . |
| WO 93/22362 | 11/1993 | WIPO . |
| WO 95/23175 | 8/1995 | WIPO . |

*Primary Examiner*—Terressa Mosley
*Attorney, Agent, or Firm*—Pennie & Edmonds LLP

[57] ABSTRACT

The invention relates to new polyesters of a polyol containing substituents with electrolyte properties with polymeric hydroxycarboxylic esters, their method of preparation and their use. The polyesters are particularly suitable for use in the preparation of sustained-release drugs.

27 Claims, 3 Drawing Sheets

POLYESTERS OF A POLYHYDROXYCARBOXYLIC ACID AND A POLYOL HAVING A SUBSTITUENT WITH ELECTROLYTE PROPERTIES

FIELD OF THE INVENTION

The invention concerns new polyesters consisting of a polyol containing substituents with electrolyte properties with polymeric hydroxycarboxylic acid esters, their production and use.

In particular, it concerns new branched-chain esters from a polyol containing substituents with electrolyte properties with groups consisting of polylactic or copolylactic-glycolic acid, their production and use as a matrix material for depot forms containing pharmacologically active substances.

BACKGROUND OF THE INVENTION

Depot forms can be administered in different ways, for example, orally, parenterally, ocularly, pulmonally or by sprinkling in wounds. Depot forms, also referred to as parenteral slow-release forms, appropriate for parenteral administration are of particular interest.

Parenteral slow-release forms can be formulated as microparticles, implants and fibers. Microparticles are of special interest, since, because of their limited dimensions, they can be suspended in an appropriate medium and administered comparatively painlessly by means of a syringe via an injection needle with limited diameter.

Such formulations are of interest for all pharmacologically active substances if long-persisting, uniform systemic or local active ingredient concentrations are desired. They are particularly advantageous for active ingredients that are destroyed or insufficiently resorbed during oral administration and can only be applied parenterally. This is the case, for example, in pharmacologically active peptides, like peptide hormones or proteins.

Of special interest are interleukins (IL-1 to IL-15), interferons (IFN), neurotrophins (NT-1 to NT-3), colony-stimulating factors (CSF), epidermal growth factors (EGF), neuronal growth factors, prolactin, luteinizing-hormone-releasing hormone (LH-RH), insulin, somatostatin, glucagon, gastrin, pentagastrin, urogastrone, calcitonin, secretin, enkephalins, endorphins, angiotensins, renin, bradykinin, tyrocidine, gramicidins, erythropoetin (EPO), angiopeptin, hirudin, oxytocin, vasopressin, calcitonin-gene-related peptide (CGRP), brain-derived growth factors (BDGF), their synthetic analogs and modifications, as well as their pharmacologically active fragments.

Generally the most constant possible active ingredient release over the entire release period is aimed for in parenteral slow-release formulations. Release of the active ingredients from depot forms made of biodegradable matrix polymers is dictated by their diffusion rate in the polymer and their degradation rate. To avoid accumulation of the matrix polymer during successive application this should be degraded as fully as possible after completion of active ingredient release.

Biodegradable matrix polymers for active ingredient embedding have already been described in 1973 in U.S. Pat. No. 3,773,919. Polymers from hydroxycarboxylic acids, especially lactic and/or glycolic acid were proposed. Polymers from lactic and/or glycolic acid are hydrolyzed in the body to lactic and/or glycolic acid, which are further metabolized to $CO_2$ and water and are therefore particularly usable in the production of parenteral slow-release forms.

Depot forms from polylactic acid (PLA) or polylactic-glycolic acid (PLGA), especially microparticles, generally exhibit a multiphase release trend and initially display a sharply increased release because of active ingredient present on the surface. This is followed by a phase of sharply reduced or nonexistent release, especially in peptide active ingredients, which is then followed by later active ingredient liberation supported by polymer mass degradation. Polymer residues are still present at the time of completion of active ingredient liberation.

EP 0 058 481 B1 describes the use of a mixture of PLGA having different molecular weights. Liberation is supposed to be linearized by this and the degradation rate adjusted to the liberation period. Use of such polymer mixtures, however, imposes high requirements on the hydrolysis stability of the active ingredient and they are not suitable for the production of microparticles.

EP 0 407 617 describes a biocompatible polyester with increased hydrolysis rate consisting of saccharides bonded to PLA or PLGA. The polyesters are proposed as matrix material for depot forms but a corresponding practical example is not included.

If depot forms can be produced with these polymers, it does appear possible to develop more rapidly degradable depot forms, but the problem of nonuniform active ingredient liberation and especially the problem of the initial burst effect persist.

DE 34 30 852 A1 describes esters from polyols and poly- or copolylactic acid, which are also proposed as matrix polymers for depot forms. Example 26 entails in-vitro liberation of washed microparticles containing bromocryptin mesylate produced by spray drying. Despite washout of the active ingredient adhering to the microparticle surface, after 24 hours 62% of the active ingredient load had already been liberated.

Slow-release forms with sufficiently high active ingredient load often cannot be produced with the known matrix polymers. However, high active ingredient load of slow-release forms is desirable, since the amount to be administered in each case is limited by its intramuscular or subcutaneous administration and the long application intervals sought for slow-release forms often can only be achieved in this manner.

However, an increase in active ingredient load generally leads to insufficient retardation, depending on the physico-chemical properties of the active ingredient. Hydrophilic active ingredients in particular, for example, those present in dissociated form under physiological conditions, therefore cannot be used in the required high concentration in the known matrix polymers and exhibit nonuniform active ingredient release, especially an increased initial active ingredient release (burst effect).

It was therefore the task of the present invention to offer matrix polymers that do not exhibit the described problems. The matrix polymers were to permit high active ingredient load and liberate the active ingredients in delayed fashion without fluctuations. The rate and overall duration of polymer degradation has to be adjusted to the rate and duration of active ingredient release so that after the end of release another dose of the depot form can be administered without running the risk of accumulation of the matrix polymer in the body.

DESCRIPTION OF THE INVENTION

Figure 1:
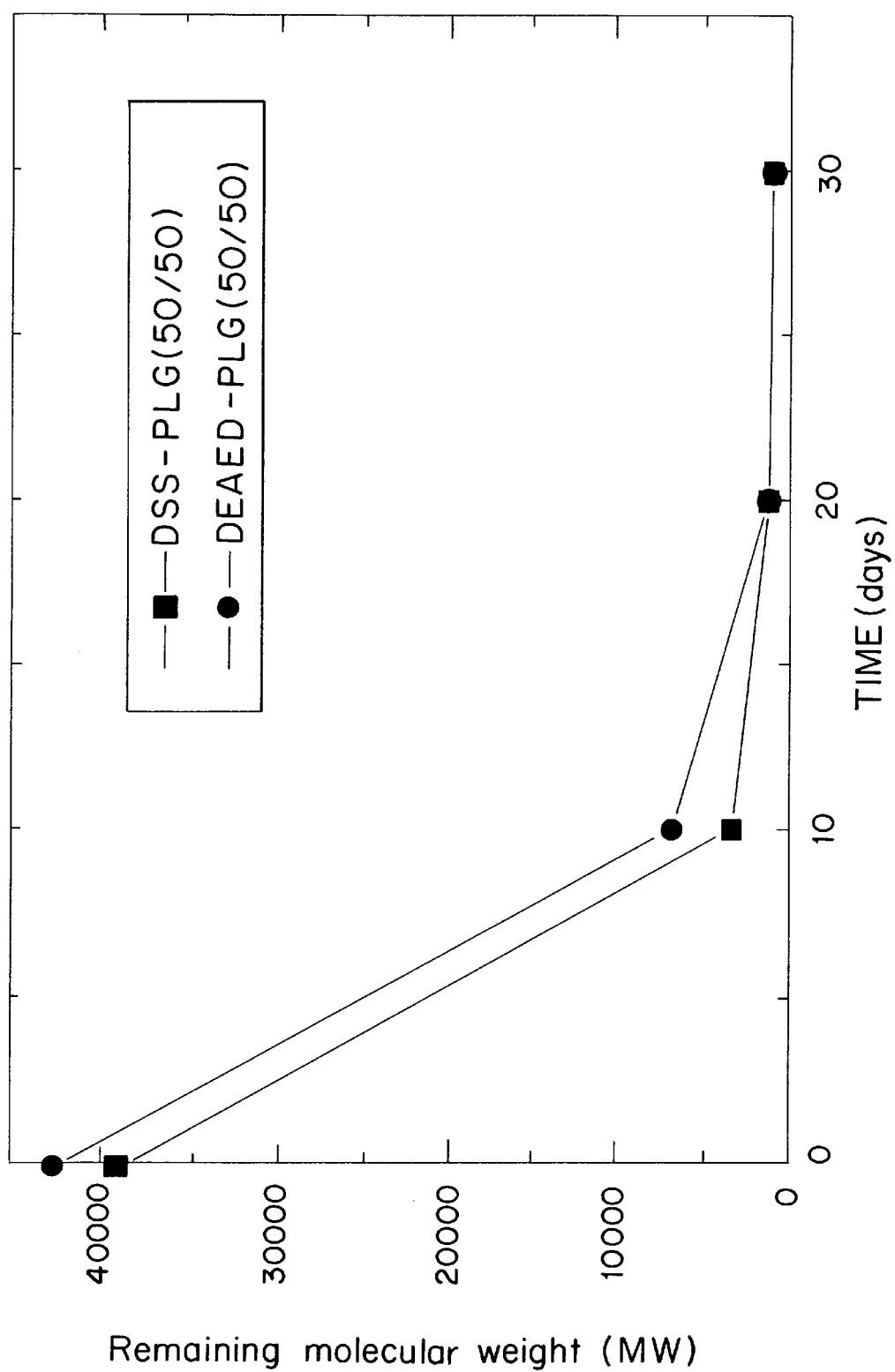
FIG. 1 is a graph of Remaining Molecular Weight (MW) plotted against Time (days) which depicts the molecular weight degradation of polymer films produced from polymers 2 and 3 described in Table 1.

The matrix polymers according to the invention can be readily processed to depot forms. They exhibit good particle formation properties in the known processes, like solvent evaporation or spray drying, and are particularly suitable for production of microparticles.

The object of the invention is a branched-chain ester from a polyol containing at least one substituent with electrolyte properties with acid groups, consisting of polyhydroxycarboxylic acids having a molecular weight to 500,000.

Substituents with electrolyte properties are understood to mean those present at least partially in the dissociated form in the hydrophilic medium.

The object of the invention is also a reaction product from a polyol containing at least one substituent with electrolyte properties with acid groups consisting of polyhydroxycarboxylic acids having a molecular weight to 500,000.

The substituents contained in the polyesters according to the invention with electrolyte properties can be formed from a strong or weak acid or a strong or weak base and can also be present in the form of their salts. They preferably consist of a strong acid or a weak base and are present in the form of their salts.

The object of the invention is therefore also a product in which the substituent exhibiting electrolyte properties is formed from a sulfo group, a primary, secondary or tertiary amine or a carboxyl group.

The polyol containing substituents with electrolyte properties can consist of the same or different alicyclic or aliphatic units linked to each other in chain-like fashion and exhibit a linear or cyclic structure.

Such polyols can be appropriately substituted poly- or oligomers of carbohydrates, for example, inulin, dextrans, xylans, cyclodextrins or consist of appropriately substituted polymers from the same or different alkene units, like substituted polyvinyl alcohol or copolymers from substituted or unsubstituted polyvinyl alcohol or acetylated polyvinyl alcohol partially acetylated with acrylic acid, α- or β-methacrylic acid, acrylamine, α- or β-methacrylamine, acrylonitrile or α- or β-methacrylonitrile.

Dextran sulfate, diethylaminoethyldextran, xylan sulfate, diethylaminoethylxylan, cyclodextrin sulfate, partially sulfonated polyvinyl alcohol, copolymers of partially sulfonated polyvinyl alcohol, polyvinyl alcohol or polyvinyl alcohol partially acetylated with acrylic acid, acrylamine, acrylonitrile, α- or β-methacrylic acid, α- or β-methacrylamine or α- or β-methacrylonitrile, as well as their salts, are preferred. The corresponding alkali salts, especially Na salts, and their halogen salts, especially chlorides, are particularly preferred.

Sulfonated polyvinyl alcohol or its copolymers can be produced by sulfonating the corresponding polyvinyl acetate or its copolymers by alcoholysis in an appropriate alcohol (for example ethanol) containing $H_2SO_4/SO_3$, followed by neutralization. If the reaction is run in, say, ethanol containing 5% $H_2SO_4/SO_3$, and neutralized, about 20% of the hydroxyl groups will become sulfonated.

Copolymers containing polyvinyl alcohol or partially acetylated polyvinyl alcohol can be produced by acid or alkaline hydrolysis of the corresponding copolymer containing polyvinyl acetate.

The polymeric hydroxycarboxylic acid groups can be constructed from one, two, three or more specific hydroxycarboxylic acids. Examples of hydroxycarboxylic acids that can be used according to the invention are lactic acid, glycolic acid, β-hydroxypropionic acid, β-hydroxybutyric acid, δ-hydroxyvaleric acid or ε-hydroxycaproic acid.

Polyhydroxycarboxylic acids from lactic and/or glycolic acid are preferred. Copolymers from lactic and glycolic acid whose acid groups consist of 25 to 50 mol % glycolic acid units are particularly preferred.

The lactic acid units can be present in the optically pure form (D- or L-lactic acid) or as the mixtures of the isomers.

The substituted polyol esters according to the invention can be produced by converting an appropriately substituted polyol with one or more hydroxycarboxylic acid(s) in the dimeric or lactone form in the presence of a catalyst suitable for ring-opening polymerization, for example, tin, zinc, tin chloride, zinc chloride, titanium tetrachloride, aluminum chloride, tin octoate or aluminum triisopropyl oxide. Tin octoate or aluminum triisopropyl oxide are preferably used.

For polymerization, the reaction components are mixed together and with the catalyst and reacted at elevated temperature.

The compounds formed according to the invention can be isolated and purified in the known manner. They are particularly suitable as a depot matrix material for drugs.

The practical examples explain the invention without representing a limitation.

EXAMPLES

Production of Branched-Chain PLGA with Dextran Sulfate-Na (DSS) as Backbone Material

Example 1

28 g D,L-lactide (LA), 22 g glycolide (GA) and 0.5 g DSS (Sigma, Mw 500,000) with one to two $SO_3$ groups per monomer were introduced into a 100 mL nitrogen flask, scavenged with nitrogen and heated in an oil bath temperature controlled to 170° C. under a nitrogen atmosphere until the monomers melted. 200 mg tin octoate was then injected into the melt during continuous agitation and, after half an hour, the reaction temperature was reduced to 150° C., where the reaction was continued for another 3.5 hours. After cooling to room temperature, the product was dissolved in 100 mL methylene chloride and washed three times with distilled water to eliminate DSS residues. The polymer solution was then filtered through a glass suction filter (#3), the product precipitated in ethanol and dried to constant weight for a few days in vacuum.

Production of Branched-Chain PLGA with Diethylaminoethyldextran (DEAED) as Backbone Material

Example 2

28 g D,L-lactide (LA), 22 g glycolide (GA) and 0.5 g DEAED (Sigma, Mw 500,000) with one to two amino groups per monomer were introduced into a 100 mL nitrogen flask, scavenged with nitrogen and heated to 150° C. in an oil bath under a nitrogen atmosphere until the monomers melted. 200 mg tin octoate was then injected into the melt during continuous agitation and the reaction run for 4 hours at 150° C. After cooling to room temperature, the product was dissolved in 100 mL methylene chloride and washed three times with distilled water to eliminate DEAED residues. The polymer solution was then filtered through a glass suction filter (#3), the product precipitated in ethanol and dried to constant weight for a few days in vacuum.

Production of Branched-Chain PLGA with a Copolymer from Partially or Fully Hydrolyzed Polyvinyl Acetate and Crotonic Acid (β-Methacrylic Acid) as Backbone Polymer (PVAcCA)

1. Hydrolysis of poly(vinyl acetate-cocrotonic acid) (PVAcCA)

a) Basic hydrolysis 2 g PVAcCA was dissolved in 100 mL methanol at 40° C. and mixed with 1 mL of aqueous NaOH solution (40%), whereupon poly(vinyl alcohol-cocrotonic acid) precipitated within 2 to 3 minutes. After half an hour, the product was filtered off, washed a few times with methanol, extracted for 5 hours in a Soxhlet device with methanol and dried. A white product with a degree of saponification greater than 99.5% was obtained.

b) Acid hydrolysis 2.6 g PVAcCA was dissolved in 100 mL methanol at 50° C. and 5 mL of 50% sulfuric acid was slowly added dropwise over 30 minutes during agitation. After 30 to 80 minutes, the product was filtered off, extracted for 5 hours in a Soxhlet device and dried. A white product was obtained that had a degree of saponification of 50 to 90% depending on the reaction time.

2. Copolymerization of PVAcCA with PLGA 28 g D,L-lactide (LA), 22 g glycolide (GA) and 0.5 g PVAcCA were introduced into a 100 mL nitrogen flask, scavenged with nitrogen and heated to 150–200° C., depending on the degree of hydrolysis, in an oil bath under a nitrogen atmosphere until the monomers melted. 200 mg of tin octoate was then injected into the melt during continuous agitation and the reaction first run for a half-hour at 170° C. and then for 3.5 hours at 150° C. After cooling to room temperature the product was dissolved in 100 mL methylene chloride and washed three times with distilled water to eliminate PVAcCA residues. The polymer solution was then filtered through a glass suction filter (#3), the product precipitated in ethanol and dried to constant weight for a few days in vacuum.

The produced esters were dissolved in $CDCl_3$ and characterized by NMR spectroscopy at 25° C. with addition of tetramethylsilane (TMS) as a reference.

$^1$H-NMR spectrum

DSS:

d=1.5–1.7 H atom of the —$CH_3$ group of the lactyl unit d=3.8–4.7 Four peaks of equal intensity: H atoms on the dextran sulfate ring The fifth H atom is covered by the glycolyl $CH_2$ peak d=4.7–4.9 H atom of the $CH_2$ group of the glycolyl unit d=5.3 H atom of the —$CH_2OSO_3Na$, covered by the —CH of the lactyl unit (lies at d=3.0 for dextran, i.e., for —$CH_2OH$)

d=5.0–5.4 H atom of the —CH group of the lactyl unit

DEAED:

d=1.2–1.4 H atom of the —$CH_3$ group of the DEAE residue d=3.1–4.0 Series of peaks: four H atoms on the dextran ring, 10 H atoms on the —$CH_2$ group in the DEAE residue and on the dextran ring d=4.9 H atom on Cl in the dextran ring covered by the —$CH_2$ peak of the glycolyl unit Remainder as above, except for d=5.3.

The molecular weights of the produced esters were determined by gel permeation chromatography in methylene chloride. The determination was carried out in a temperature-controlled column combination (Lichrogel PS mix and Lichrogel PS 40, 10 μm, Merck) at 25° C. using a differential refractometer (Merck Hitachi RI-71). Polystyrene standards were used for calibration (Merck, Mw 3250; 5100; 19,600; 34,500 and 87,000).

Polymer degradation in vitro

Production of test samples

To investigate the degradation behavior of the polymers according to the invention, 10% (W/V) polymer solutions in methylene chloride were produced. These were cast onto teflon-coated plates and the solvent eliminated first for 48 hours at room temperature then in vacuum at room temperature. After drying to constant weight, 100–200 μm thick films were obtained that were cut into 20 mm×10 mm pieces.

Molecular weight degradation

Four to 6 of the polymer film pieces produced in this manner were introduced into 50 mL of distilled water, the temperature of which was controlled at 37° C., removed after established time intervals, dried to constant weight in vacuum at room temperature and investigated by gel permeation chromatography with respect to changes in molecular weight. FIG. 1 depicts the molecular weight degradation of polymer films produced from polymers 2 and 3.

Polymer weight loss

Figure 2:
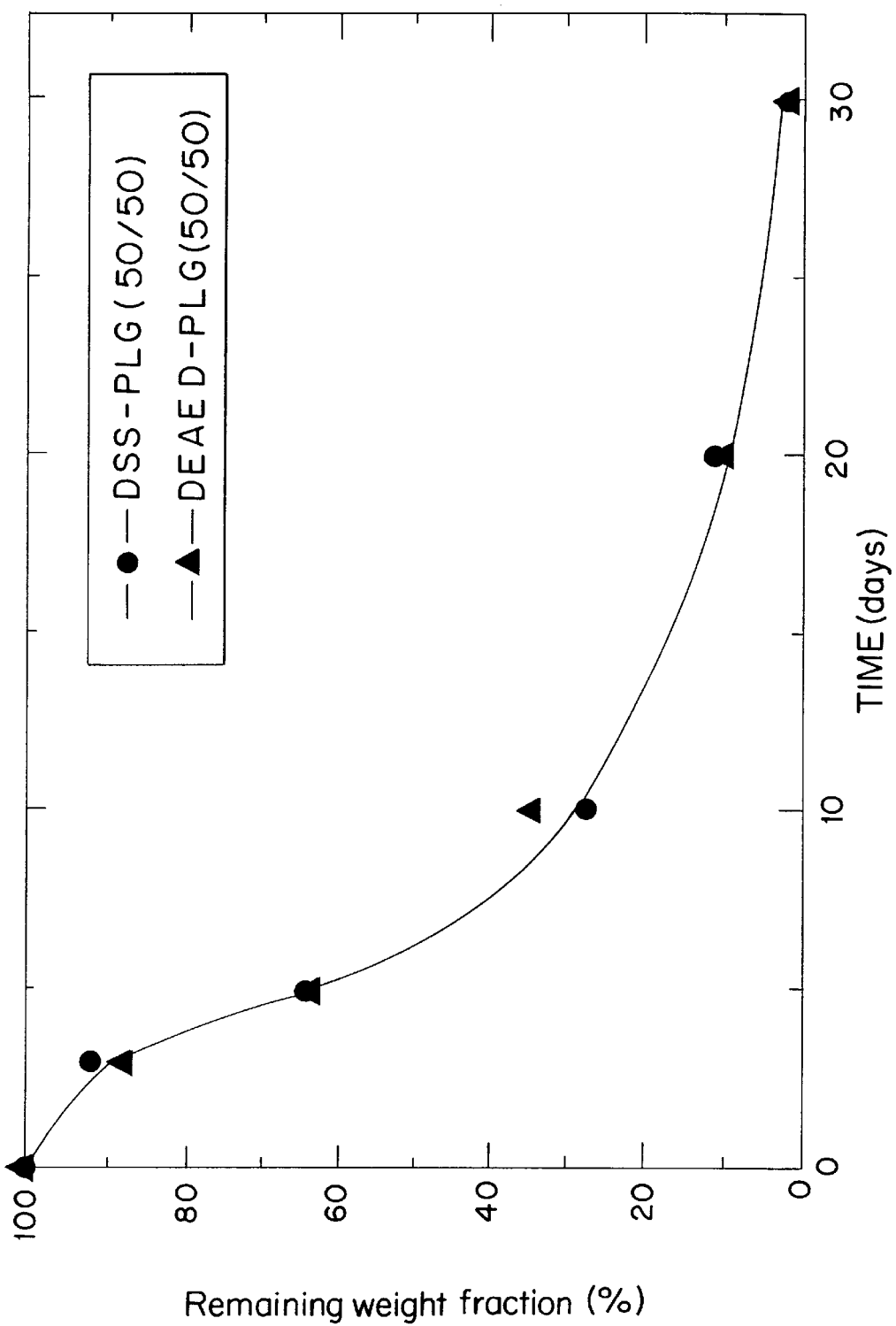
FIG. 2 is a graph of Remaining Weight Fraction (%) plotted against Time (days) which depicts the polymer weight loss of polymer films produced from polymers 5 and 13 described in Table 1.

The weight loss was determined gravimetrically. For this purpose, a polymer film piece was introduced into a nylon gauze and this was sealed by heating and transferred to a shaker bath filled with distilled water, thermostated to 37° C. After fixed time intervals, the gauze was removed, dried to constant weight in vacuum at room temperature and the remaining weight determined. FIG. 2 shows a graph of the polymer weight remaining after the corresponding time intervals of polymer films produced from polymers 5 and 13 (Table 1).

The polymers according to the invention exhibit significantly increased molecular weight degradation in comparison with ordinary linear polylactide-coglycolides, which is accompanied by an also significant weight loss of the polymer.

Production of microparticles loaded with bovine serum albumin (BSA)

Microparticles were produced from polymers 5 and 13 (Table 1) by solvent evaporation. For this purpose a BSA solution (25%) was introduced into a 20% polymer solution (methylene chloride) during intense homogenization with a toothed-rim dispersal rod so that BSA and polymer were in a weight ratio of 10%. This emulsion was injected under agitation into a 0.5% PVA solution from which the formed microparticles were filtered off after 3 hours of agitation. After drying (in vacuum at room temperature) the microparticles were stored at 5° C.

The BSA degree of loading of the microparticles was determined photometrically at 278 nm after dissolution in acetonitrile and extraction with water. The particle size was determined by laser light scattering. The obtained results are summarized in Table 2.

Active ingredient release in vitro

About 100 mg of microparticles (accurately weighed) was transferred to sealable reagent test tubes (20 mL) and mixed with 5 mL phosphate buffer solution (pH 7.2). The sealed test tubes were agitated at 37° C. in a rotating metal block thermostat (Rotatherm) at 15 rpm. After predetermined time intervals the microparticles were centrifuged at 4000 rpm for 30 minutes, 3 mL of sample solution was taken, replaced with fresh phosphate buffer solution (pH 7.2) and liberation continued. The BSA concentration in the sample solution was determined photometrically at 278 nm.

Figure 3:
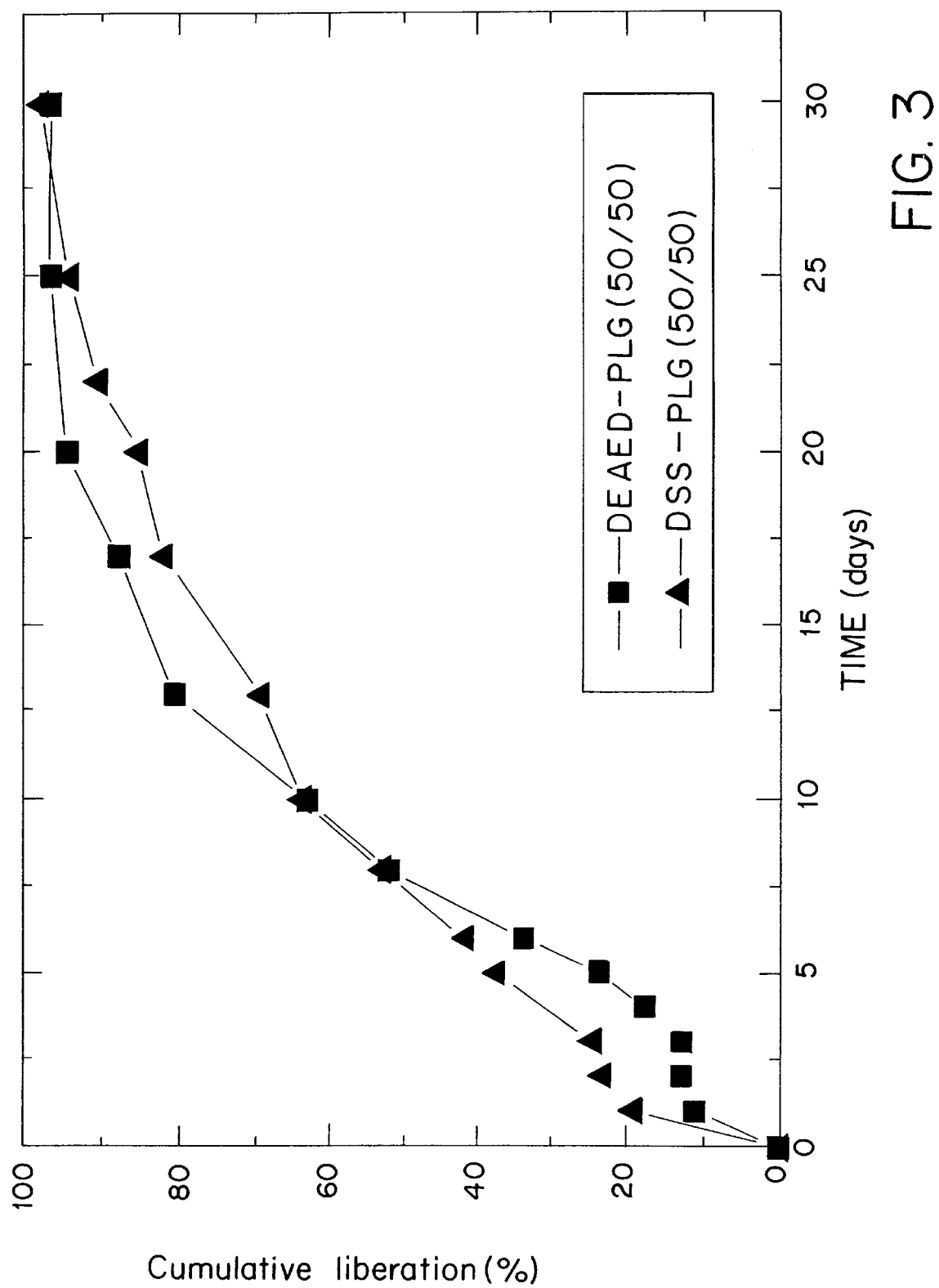
FIG. 3 is a graph of Cumulative Liberation (%) plotted against Time (days) for polymers 5 and 13 described in Table 1.

FIG. 3 shows the results of the liberation investigations. It is obvious that the increase in percentage of dextran sulfate sodium in the polymer leads to a reduction in the initially increased liberation and this occurs almost constantly over the entire liberation period. This is in distinct contrast to the generally two-phase liberation behavior of linear polylactide-coglycolides, which is marked by a high burst effect and delayed active ingredient liberation.

A comparison of the liberation behavior of the polymers according to the invention with their weight loss (cf. FIG. 2) also shows that the former runs essentially parallel to the latter. The liberation behavior therefore appears to be largely controlled by the weight degradation of the matrix polymer. The polymers according to the invention are therefore particularly suited for formulation of depot forms.

TABLE 1

| No. | Backbone | Monomer LA:GA | Tin octoate/DSS[a]/M (mol/mol/mol) | T(°C.) | t(h) | Mw | Mw/Mn |
|---|---|---|---|---|---|---|---|
| 1 | Dex—SO$_3$Na | 50/50 | 2.3/14/1000 | 170 | 24 | 32.000 | 2.33 |
| 2 | Dex—SO$_3$Na | 50/50 | 5.3/14/1000 | 200 | 8 | 33.000 | 2.80 |
| 3 | Dex—SO$_3$Na | 50/50 | 1.8/14/1000 | 170 | 24 | 44.000 | 2.22 |
| 4 | Dex—SO$_3$Na | 50/50 | 1.2/14/1000 | 170 | 12 | 48.000 | 2.47 |
| 5 | Dex—SO$_3$Na | 50/50 | 1.8/14/1000 | 170 | 12 | 39.100 | 2.48 |
| 6 | Dex—SO$_3$Na | 50/50 | 0.42/7.2/1000 | 170 | 4 | 43.000 | 2.15 |
| 7 | Dex—SO$_3$Na | 50/50 | 0.85/3.0/1000 | 170 | 4 | 62.000 | 1.93 |
| 8 | Dex—SO$_3$Na | 50/50 | 0.85/1.5/1000 | 170 | 4 | 76.000 | 1.68 |
| 9 | Dex—SO$_3$Na | 50/50 | 0.85/4.4/1000 | 170 | 4 | 54.000 | 2.15 |
| 10 | Dex—SO$_3$Na | 50/50 | 1.8/1.5/1000 | 170 | 4 | 94.000 | 1.40 |
| 11 | Dex—SO$_3$Na | 75/25 | 1.3/7.5/1000 | 170 | 4 | 38.000 | 1.84 |
| 12 | Dex—SO$_3$Na | 100/0 | 1.3/7.6/1000 | 170 | 4 | 37.000 | 1.87 |
| 13 | DEAE—Dex | 50/50 | 1.8/12/1000 | 150 | 12 | 42.500 | 2.19 |
| 14 | DEAE—Dex | 50/50 | 1.8/14/1000 | 150 | 12 | 40.000 | 2.06 |
| 15 | DEAE—Dex | 75/25 | 1.8/7.8/1000 | 150 | 4 | 77.000 | 2.47 |
| 16 | DEAE—Dex | 100/0 | 1.8/7.8/1000 | 150 | 4 | 87.000 | 2.67 |

[a]or DEAE—Dex., referred to one ring unit.

TABLE 2

| No.* | LA/GA (mol) | BSA (wt %) | Average diameter (µm) | Field (%) |
|---|---|---|---|---|
| 5 | 50/50 | 6.3 | 40 | 86 |
| 13 | 50/50 | 6.0 | 40 | 89 |

*Same numbering as Table 1.

We claim:

1. A branched-chain ester comprising a polyhydroxycarboxylic acid which comprises at least one hydroxycarboxylic acid, and a polyol having at least one substituent with electrolyte properties, said ester having an average molecular weight of up to about 500,000.

2. The ester of claim 1, wherein said hydroxycarboxylic acid is lactic acid, glycolic acid, β-hydroxy-propionic acid, β-hydroxy-butyric acid, δ-hydroxy-valeric acid, ε-hydroxy-caproic acid or a mixture thereof.

3. A reaction product of at least one hydroxycarboxylic acid and a polyol, wherein the polyol has at least one substituent with electrolyte properties, and is polymerized to provide an average molecular weight of up to about 500,000 for the product.

4. The ester of claim 1 in which the substituent with electrolyte properties is a sulfo group, a carboxyl group or a primary, secondary or tertiary amine.

5. The reaction product of claim 3 in which the substituent with electrolyte properties is a sulfo group, a carboxyl group or a primary, secondary or tertiary amine.

6. The ester of claim 4 in which the polyol having at least one substituent with electrolyte properties is present as an alkali metal or halide salt.

7. The reaction product of claim 5 in which the polyol having at least one substituent with electrolyte properties is present as an alkali metal or halide salt.

8. The ester of claim 1 in which the polyol is dextran sulfate; diethylaminoethyldextran; xylan sulfate; diethylaminoethylxylan; cyclodextrin sulfate; partially sulfonated polyvinyl alcohol; or a copolymer of partially sulfonated polyvinyl alcohol, polyvinyl alcohol or polyvinyl alcohol partially acetylated with acrylic acid, acrylamine, acrylonitrile, α- or β-methacrylic acid, acrylamine, or α- or β-methacrylonitrile.

9. The reaction product of claim 3 in which the polyol is dextran sulfate; diethylaminoethyldextran; xylan sulfate; diethylaminoethylxylan; cyclodextrin sulfate; partially sulfonated polyvinyl alcohol; or a copolymer of partially sulfonated polyvinyl alcohol, polyvinyl alcohol or polyvinyl alcohol partially acetylated with acrylic acid, acrylamine, acrylonitrile, α- or β-methacrylic acid, acrylamine, or α- or β-methacrylonitrile.

10. The ester of claim 1 wherein the polyhydroxycarboxylic acid is polylactic acid or a copolymer of lactic and glycolic acid.

11. The reaction product of claim 3 wherein the polyhydroxycarboxylic acid is polylactic acid or a copolymer of lactic acid and glycolic acid.

12. The ester of claim 10 wherein the copolymer of lactic acid and glycolic acid comprises 25 to 50 mole % of glycolic acid units.

13. The reaction product of claim 11 wherein the copolymer of lactic acid and glycolic acid comprises 25 to 50 mole % of glycolic acid units.

14. A depot matrix for the controlled release of a drug, comprising the ester of claim 1.

15. A depot matrix for the controlled release of a drug, comprising the reaction product of claim 3.

16. A depot matrix for the controlled release of a drug, comprising the ester of claim 10.

17. A depot matrix for the controlled release of a drug, comprising the reaction product of claim 11.

18. A composition for the controlled release of a drug comprising a matrix of the ester of claim 1 in combination with a drug.

19. A composition for the controlled release of a drug comprising a matrix of the reaction product of claim 3 in combination with a drug.

20. A composition for the controlled release of a drug comprising a matrix of the ester of claim 10 in combination with a drug.

21. A composition for the controlled release of a drug comprising a matrix of the reaction product of claim 11 in combination with a drug.

22. The reaction product of claim 3, wherein said hydroxycarboxylic acid is lactic acid, glycolic acid, β-hydroxypropionic acid, β-hydroxybutyric acid, δ-hydroxyvaleric acid, ε-hydroxycaproic acid or a mixture thereof.

23. The composition of claim 18, 19, 20 or 21 wherein the drug is selected from interleukins (IL-1 to IL-15), interferons (IFN), neurotrophins (NT-1 to NT-3), colony-stimulating factors (CSF), epidermal growth factors (EGF), neuronal growth factors, prolactin, luteinizing-hormone-releasing hormone (LH-RH), insulin, somatostatin, glucagon, gastrin, pentagastrin, urogastrone, calcitonin, seretin, enkephalins, endorphins, antiotensins, renin, bradykinin, tyrocidin, gramicidins, erythropoetin (EPO), angiopeptin, hirudin, oxytocin, vasopressin, calcitonin-gene-related peptide (CGRP), brain-derived growth factors (BDGF), their synthetic analogs and modifications, and their pharmacologically active fragments.

24. The ester of claim 1 wherein the polyhydroxycarboxylic acid is a copolymer of lactic acid and glycolic acid.

25. The ester of claim 24 wherein the polyol is dextran sulfate.

26. The ester of claim 24 wherein the polyol is diethylaminoethyl dextran.

27. The ester of claim 24 wherein the polyol is partially or fully hydrolyzed polyvinylacetate-crotonic acid.

* * * * *